United States Patent [19]
Modliszewski et al.

[11] Patent Number: 5,498,436
[45] Date of Patent: Mar. 12, 1996

[54] COPROCESSED GALACTOMANNAN-GLUCOMANNAN

[75] Inventors: James J. Modliszewski, Brick, N.J.; Arthur D. Ballard, Friendship, Me.

[73] Assignee: FMC Corporation, Philadelphia, Pa.

[21] Appl. No.: 176,163

[22] Filed: Dec. 30, 1993

[51] Int. Cl.$^6$ .................... A23L 1/0526; A23L 1/0528
[52] U.S. Cl. ............... 426/573; 426/579; 426/658; 426/589; 426/605; 426/603
[58] Field of Search .................... 426/573–579, 426/658, 589, 605, 603

[56] References Cited

U.S. PATENT DOCUMENTS

| | | | |
|---|---|---|---|
| 2,466,146 | 4/1949 | Baker | 426/573 |
| 3,808,195 | 4/1974 | Shelso et al. | 260/209 |
| 4,200,661 | 4/1980 | Brigand et al. | 426/573 |
| 4,427,704 | 1/1984 | Cheney et al. | 426/104 |
| 4,746,528 | 5/1988 | Prest et al. | 426/573 |
| 4,894,250 | 1/1990 | Musson et al. | 426/573 |
| 4,952,686 | 8/1990 | Renn et al. | 426/573 |
| 5,213,834 | 5/1993 | Ikeda et al. | 426/573 |

OTHER PUBLICATIONS

Lebensmittel Wissenschaften und Technologies 11:279–282 (1978).
Journal App. Phycol. 4:347–351 (1992).
Sen–I Gakkaishi 48:437–440.
Food Hydrocolloids $_c$:199–222 (1992).
Gums and Stabilizers of the Food Industry 5, Phillips et al., eds. Oxford University Press, Oxford, England 563–569 (1987).
Bulletin Chem. Soc. Japan 45:561 (1972).

*Primary Examiner*—Jeanette Hunter
*Attorney, Agent, or Firm*—Mark A. Greenfield; Robert L. Andersen; Polly E. Ramstad

[57] ABSTRACT

A composition comprising: (A) a coprecipitate consisting essentially of: (a) a galactomannan, with (b) a glucomannan; and (B) optionally, a gelling agent admixed with the formed coprecipitate. The inventive compositions are useful as the base for food products such as: a gelled or thickened food, a pourable salad dressing; a liquid food or food additive, a food spread such as a margarine or cheese spread, a water dessert gel, a mayonnaise, a frozen dessert, and the like.

31 Claims, 1 Drawing Sheet

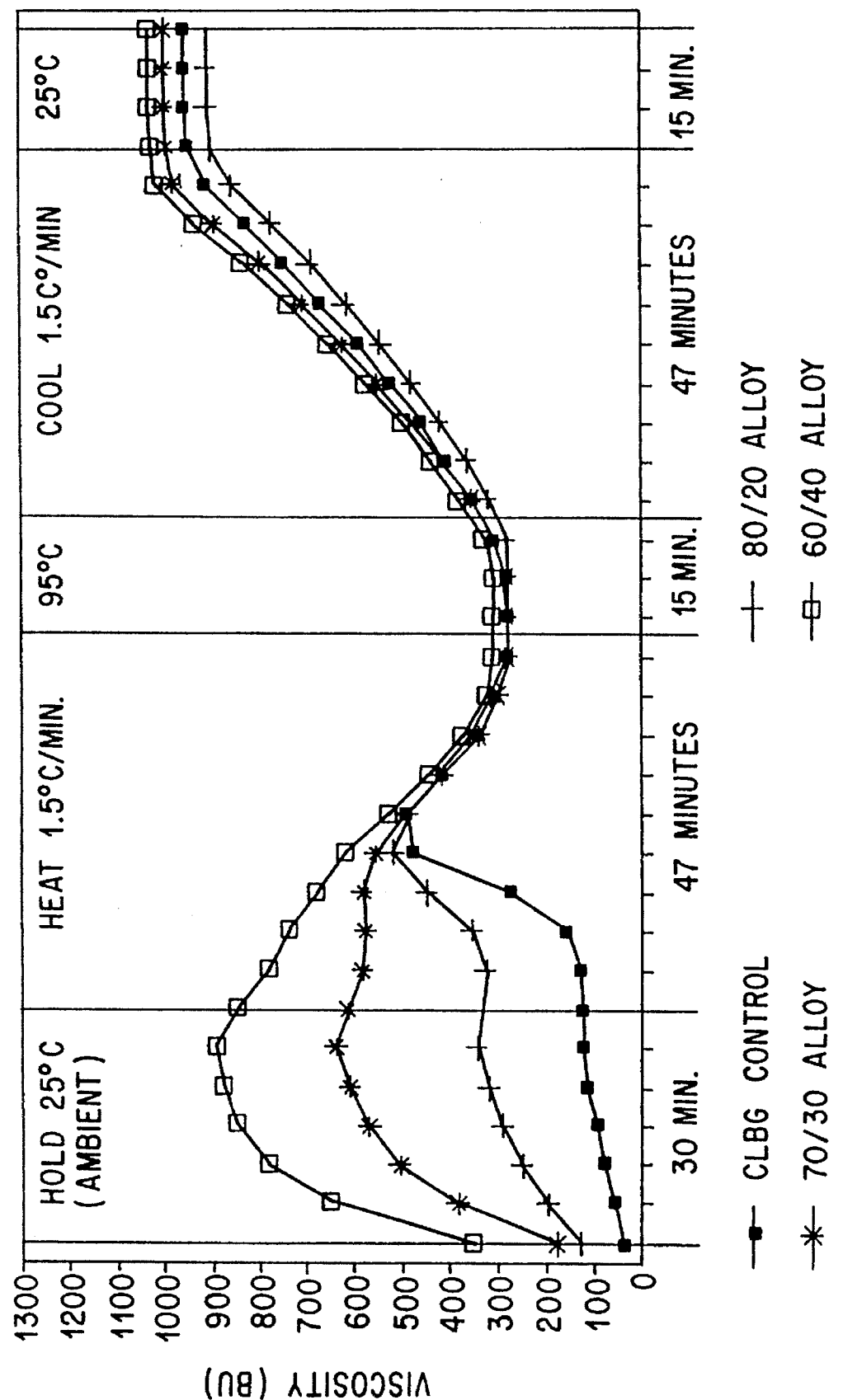

COPROCESSED GALACTOMANNAN-GLUCOMANNAN

BACKGROUND OF THE INVENTION

1. Field of the Invention

This invention relates to coprocessed (coprecipitated) combinations of at least one galactomannan (preferably locust bean gum) and at least one glucomannan (preferably konjac). In a further embodiment, the inventive galactomannan-glucomannan coprecipitate may be mixed with a gelling agent (preferably a carrageenan) to form a complex hydrogel. Both the coprecipitate and the complex hydrogel may be used as bases in water dessert gels and other foods.

2. Description of the Related Art

Land plant-derived polymannan gums (galactomannans or glucomannans) such as locust bean gum (LBG) or konjac gum are known for use by themselves or in combination with hydrocolloids such as agar, carrageenan, and xanthan gum to form gels of various textures which are used, for example, in the food industry. Of particular note are carrageenan-based systems conventionally prepared by simply admixing purified or crude carrageenan-reactive polymannan gum with a carrageenan gelling agent, especially kappa carrageenan, to provide gels widely used as thickeners or gelling agents for prepared foods. Both the single-system and mixed-system gels have other interesting and useful properties including water-binding capacity and the ability to stabilize polyphase systems such as emulsions and suspensions.

Highly-refined mixed gel systems of known types intended for use in demanding food applications such as water-based dessert gels, are commercially dependent upon convenient and economical extraction/purification/clarification techniques for obtaining a polymannan gum component substantially free of impurities, and upon good interreaction of the product with the selected gelling agent to produce clear, stable gels. Accordingly, a popular commercial water gel dessert system is one based on clarified LBG (cLBG) and carrageenan. LBG is readily clarified by extracting the water-soluble locust bean gum from its source, usually at elevated temperatures, into aqueous medium, followed by filtration and precipitation of the extract; the cLBG is then admixed with carrageenan, typically kappa carrageenan, with which it interreacts quite well. The interreacted gum enhances the strength of the resulting gel, so that the desired gelling or suspending effect of the product can be obtained with significantly less carrageenan ingredient than would be required if the carrageenan were to be used alone.

Galactomannan-based gel systems have their limitations, however. Typically, cLBG or other clarified galactomannan gum is dried and ground for storage after final recovery from the purification solution; the dried gum is then resolubilized for use. Since dried LBG and some other galactomannans commonly used in these systems are not readily soluble in cold water (see, e.g., U.S. Pat. No. 3,808,195), the aqueous solubilizing medium must be heated to above ambient temperatures (above about 25° C.) to completely solubilize the dried gums and obtain full benefit of their properties, particularly viscosity modification and reactivity with gelling agents such as carrageenan. In the case of LBG, heating to at least about 60° C., typically to about 80° C. or more, is necessary to substantially solubilize the dehydrated purified gum for use. Otherwise, the gum fails to fully dissolve in aqueous medium, the resulting heterogeneous mixture becomes hazy on standing, and the product cannot be used where clear gels are desired. Further, optimum thickening properties of the partially solubilized gum are not realized, and reactivity is lower than with fully solubilized gum.

The use of glucomannans for applications requiring highly refined gel products is also limited. For example, konjac (*Amorphophallus rivieri*, A. konjac) is a known viscosity modifier for foods, and is also known to be interreactive with carrageenan to provide an improved mixed gel system. However, its use is substantially limited to applications which do not require extensive purification of crude konjac flour. Processing of the konjac flour to substantially remove impurities, particularly the proteinaceous material (sacs) encapsulating the glucomannan polymers as well as starch, odor and color, requires heating, which tends to deacetylate the polysaccharide gum (especially in the slightly alkaline medium which improves product gel strength). The deacetylated gum will form a gel upon cooling which does not reliquefy with heating. While this is an advantage in some food uses, for example in the production of retort-resistant foods such as traditional "konyaku" noodles, as a practical matter it precludes the use of konjac in applications requiring clear, thermoreversible gels, a frequent requirement in the food industry. Additionally, owing to its high viscosity and cellular contaminants, the purified gum, whether or not substantially deacetylated, is difficult to filter and recover. It should be noted, however, that filtration is optional where the end use of the gel does not have to be clear; thus filtration can be omitted where cost or operating efficiency is an important factor.

Both glucomannans and galactomannans are well-known, and widely used either separately or in combinations thereof as thickeners, viscosifiers, or gelling agents, particularly in the food industry. As noted above, the concept of admixing landplant-derived polymannans with each other or with seaplant-derived hydrocolloids such as carrageenan or agarose to obtain mixed gel systems having advantageous properties is known: see, for example U.S. Pat. No. 2,466,146 (1949) to Baker, describing edible gelling compositions comprising Irish moss extract and locust bean gum; Lebensmittel Wissenschaften und Technologies 11:279–282 (1978) directed to carrageenan/carob gels; Food Hydrocolloids 6:199–222 (1992) and Gums and Stabilizers of the Food Industry 5, Phillips, et al., eds, Oxford Univ. Press, Oxford, England, 563–569 (1989), describing konjac glucomannan and kappa-carrageenan compositions; J App. Phycol. 4:347–351 (1992) reporting properties of compositions of seaweed extracts including kappa carrageenan and furcelleran with either konjac flour or locust bean gum; U.S. Pat. No. 5,213,834 (1993) relating to compositions of konjac glucomannan and binders such as locust bean gum and/or carrageenan with organic acid microcapsules; U.S. Pat. No. 4,427,704 (1984) to Cheney, et al., referring to konjac/carrageenan compositions; Sen-1 Gakkaishi 48:437–440 (1992) comparing konjac mannan and hydroxypropylcellulose blends; and U.S. Pat. No. 4,952,686 to Renn, et al., (1990) referring to alloys of cassia (galactomannan) gum with one or more non-glucomannan thickening or gelling agents selected from a group including locust bean gum and carrageenan, but not konjac.

SUMMARY OF THE INVENTION

In a first embodiment this invention is a composition comprising: (A) a coprecipitate consisting essentially of: (a) a galactomannan, with (b) a glucomannan; and (B) optionally, a gelling agent admixed with the formed coprecipitate. Preferably, the galactomannan is locust bean gum and the glucomannan is derived from konjac. The gelling agent, when present, may be carrageenan, xanthan, agar, gellan, pectin, gelatin, starch, or a mixture thereof, carrageenan being preferred and may be present together with a gel-inducing-effective-amount of a gelling inducer. The inventive composition may be in dry powder form, it being a particularly useful aspect of this invention that the dry powder is substantially soluble in water at a temperature of about 18° to 23° C. (that is, in ambient or "cold" water). Another particularly useful and unexpected aspect of the present invention is that the inventive coprecipitate exhibits enhanced reactivity or miscibility with gelling agents, as compared to the unmodified gums used as starting materials. The inventive composition also may be afforded in the form of an aqueous gel, by mixing a desired amount of the dry powder with water (usually between 0.5 and 5 % by volume, based upon the gel total volume).

The glucomannan can comprise from 1 to 99, but usually comprises about 10 to 90, preferably 10 to 50, more preferably 20 to 40, most preferably 25 to 35 dry weight percent, based on the total dry weight of the polysaccharides of the coprecipitate. Where the admixed gelling agent is present, it may comprise 10 to 90, preferably 30 to 80, more preferably 40 to 70, most preferably 25 to 35 dry weight percent of the total dry weight of the polysaccharides of the admixed composition.

In another embodiment, this invention comprises a method for preparing a coprecipitate of a galactomannan with a glucomannan, such method comprising: (A) mixing a galactomannan with an aqueous medium (optionally accompanied by heat and/or agitation) to form a galactomannan sol; (B) mixing a glucomannan in similar manner with the same or another volume of the aqueous medium to form a glucomannan sol; (C) comixing the galactomannan sol and glucomannan sol (if they were initially mixed separately); (D) optionally clarifying the galactomannan sol, the glucomannan sol, or their comixture; (E) coprecipitating the comixed sols by the addition of an organic solvent that is miscible with the aqueous medium; (F) separating the coprecipitate from the aqueous medium; (G) drying the coprecipitate, and (H) optionally grinding the dried coprecipitate to a finer powder.

The inventive compositions are useful as the base for many food and industrial products such as: a gelled or thickened food; a pourable salad dressing; a liquid food or food additive; a food spread such as a margarine or cheese spread; a water dessert gel; a mayonnaise; a frozen dessert; a cosmetic or pharmaceutical liquid, cream or lotion excipient; a dental care product; an air freshener gel; a de-icing fluid; and the like. Where the compositions are used as water dessert gels, they may be in dry form as a mix, or may be in the form of aqueous gels, with or without the admixed gelling agent, and typically in admixture with one or more flavorants, colorants, sweeteners, food particles, herbs, preservatives, buffering agents, acidifying agents or gel strengtheners.

In a further embodiment, the invention affords a method for achieving the water solubility of a galactomannan gum (particularly locust bean gum) at temperatures of about 18° to 23° C. comprising coprecipitating the gum with a glucomannan gum, particularly one derived from konjac.

BRIEF DESCRIPTION OF THE DRAWING

The sole Figure is a graphical illustration of the effect of a series of temperature parameters (ambient, heat, cool) over time on the viscosity in water of the inventive locust bean gum / konjac glucomannan coprecipitate as compared to a clarified locust bean gum control.

DESCRIPTION Of THE PREFERRED EMBODIMENTS

Other than in the operating examples, or where otherwise indicated, all numbers expressing quantities of ingredients, parameters, or reaction conditions used herein are to be understood as modified in all instances by the term "about".

Starting materials for the practice of the invention comprise galactomannan and glucomannan gums of the type well-recognized in the art as useful thickeners and gelling agents.

The principal glucomannan of commerce is derived from *Amorphallus Koniac* species, and is recommended for its ready availability; it will hereinafter be referred to as "konjac-derived glucomannan", "konjac glucomannan" or by its commercial designation of "konjac". Processes for recovery of glucomannans from their source plants are well-known. Galactomannan gums for use in the invention include guar, locust bean (carob), and tara gums, as well as galactomannans from other legumes such as honey bean, flame tree, sesbania and Cassia species. The galactomannans are recovered from the seed endosperm of the plant source and purified according to known methods; galactomannan source material of any grade of purity may be used as starting material in the invention and purified as desired. Crude (native) galactomannan or glucomannan flours or gums commercially available are suitable starting materials, which may be further purified if desired, again according to techniques well-known in the art, such as those described in Bull. Chem. Soc. Jpn. 45:561 (1972) and U.S. Pat. No. 4,952,686 to Renn, et al. (1990), incorporated herein by reference.

One additional advantage of the coprocessed galactomannan/glucomannan gums of the present invention is that less clarification of the polymannan starting materials is required to obtain a clear gel system of excellent quality, eminently suitable as a base for foods such as water-gel desserts.

According to the method of the invention, the starting glucomannan and galactomannan components of the coprecipitate composition are purified as desired for the intended application. The components are then codissolved in an aqueous medium optionally containing additives, for example, flavor, color, sweetener, vitamins, proteins, preservatives, etc., in proportions ranging from about 1% to at least about 1–90, 20–50, 20–40% functional glucomannan gum, based on the total weight of the combined functional glucomannan and functional galactomannan gums, depending upon the desired properties of the coprocessed product. (The term "functional", as used above and further herein in this context, means substantially pure, that is, active gum.) Generally, and most especially with coprocessed LBG and konjac gums, proportions of the starting functional glucomannan gum component to total functional glucomannan and galactomannan gum components are at least from about 10% by weight, preferably from about 20% by weight, and most preferably from about 30% by weight, again depending upon the intended use. The cold-solubilizing power of glucomannan is not strong at proportions less than about 10% of the total gum content and for applications wherein cold-solubility of the galactomannan is important, a minimum of at least about 20% functional glucomannan gum (of the total functional gum content, by weight) should be used. As shown in the Figure, cold-solubility of LBG improves at about 30% up to about 40% functional konjac gum by total functional gum weight and proportions of at least about 30% functional glucomannan gum for such applications are accordingly preferred.

After dissolving the gum components in the aqueous medium, the gums are coprecipitated, with optional intervening conventional clarification steps which are chosen to simultaneously purify both or either of the components if necessary. The coprecipitate is then recovered by means such as filtration, usually followed by drying.

In general, a maximum total concentration of gums in the processing medium on initial mixing of no more than about 2.5% is recommended for optimum processing, and a maximum gum concentration range of from about 1.2 to 2.2% is often preferable. Where a clarified coprecipitate is desired, it is of particular importance to adjust the total gum content of the processing medium to facilitate filtration of the coprecipitated material; a total filtrate solids content of from about 0.3% to about 0.8% is desirable for ease of processing. The pH of the processing solution should be low enough to prevent gelling of the konjac component during processing; a pH of less than about 7.2, typically from about 6.6 to about 6.8 is usually suitable.

In a preferred mode of practice of the invention, the glucomannan and galactomannan components are dissolved, either separately followed by mixing, or together in the same vessel. Methods of dissolving these gums are known in the art. In particular, dissolution of many galactomannans, especially locust bean gum (LBG), requires heating.

After dissolution of the gums, and either before or after mixing if dissolved separately, it may be advantageous to filter or otherwise process the gum solution to remove impurities. This is especially important if the starting materials are crude gums or flours, and the final product is to be refined, such as a clear water dessert gel. It is known to use filtration, especially with filter aid, to remove impurities; other methods suitable to the final use of the coprecipitated gums may also be used. The details of any optional purification process are not part of the invention. It is particularly advantageous to dissolve the gums together and to purify them together if required, to minimize the number of steps required to form the final product. Unexpectedly, it was found that processing the preferred gums (LBG and konjac) together, and especially filtration, is easier to perform (lower backpressures, shorter filtration times) than with the separate gums, or with konjac alone. The molecular weights of the gums are not critical; native molecular weights are acceptable, which are approximately 1 million daltons for konjac, and 250,000 daltons for locust bean gum; partially depolymerized gums, to lower processing viscosity, are also useful, especially if the molecular weight (or its surrogate, the viscosity) is 30% or more of the native material.

As a preferred method when working with crude flours, and when clarified products are to be produced, filter aid is added to the dissolved gums, typically at a ratio of 2 parts filter aid to 1 part crude gum, and then the mixture is filtered in standard equipment, such as a plate and frame filter press.

The total gum concentration during coprocessing, and the temperature of processing, may vary according to tradeoffs known in the art. Higher gum concentrations and lower processing temperatures are advantageous in increasing process efficiency, but the same conditions raise the viscosity of the solution and make processing more difficult. The optimal balance depends on the details of the processing equipment used. Generally, temperatures higher than 60° C., which substantially lower the viscosity of these gum solutions, are preferred. Temperatures of 70°–90° C. are more preferred. Suitable total crude gum concentrations, including solids to be removed, are typically about 0.5% to 2.5% of total solids, preferably 1% to 2%, with concentrations in the higher end of this range preferred when the equipment permits.

The coprecipitation of the galactomannan and glucomannan is critical to this invention, but the manner of coprecipitation is not. Thus, coprecipitation may be by any effective means which does not result in significant separation of the gums. Examples of suitable means include coprecipitation with organic solvents, drum drying, spray drying, air drying, bead milling, fluid bed drying, and freezing followed by pressing or drying. Coprecipitation drying methods are preferred and coprecipitation with a water-miscible solvent and possible pH adjustment is more preferred. Coprecipitation with alcohols, and especially with isopropyl alcohol, is most preferred. The effective coprecipitation amount of an alcohol will vary with conditions, but addition of 2 or more volumes of azeotropic isopropanol (about 82–85% isopropanol) to one volume of gum solution is an effective precipitant. Lower ratios may be effective, depending on details of the process conditions, such as gum concentration and temperature. Lower addition ratios, such as 1.5 to 1, or to 1, are preferred when effective.

EXAMPLES

Materials Locust bean gum was obtained from Grinsted as grade LBG-A. Konjac flour was obtained from FMC Corporation, Philadelphia, Penna., U.S.A.

Example 1

A series of coprecipitates were made at various gum ratios. Crude locust bean gum and konjac flour, in weight ratios of 100:0, 90:10, 80:20, 70:30, and 60:40, were processed as follows:

Gums were dispersed in water with mechanical stirring at a total gum concentration of 2.2%, and allowed to hydrate for about 40 minutes. Then 1 volume of hot water, about 180° F. (82° C.) was added, and the mixture was stirred with heating to 85° to 88° C. for about 1 to 1.5 hours. After dissolution was complete, filter aid (Dicalite) was added at a ratio of 2:1 (based on weight of gum), and the mixture was stirred to disperse the filter aid. Then the mixture was filtered at about 70 psi (4.9 kg/sq cm) maximum pressure at a temperature of about 77° C. The clear filtrate was partially concentrated to obtain a gum concentration of about 1% (0.75–1.0%). The concentrated filtrate was mixed with 2 volumes (82%) isopropyl alcohol. The coprecipitate was separated on a screen and collected into a wash of 1 volume of 82% isopropanol. It was recovered into a Willmes press and squeezed to remove excess alcohol. The recovered product was dried to 85° C. in a rotary vacuum drier at 24–27 inches (61–69 cm) of mercury of vacuum to a final moisture content of about 5–10%, and ground to a mesh size of about 97% passing a 100 mesh screen.

The rate of development of viscosity with time was then measured for each powder, as shown in the Figure. Viscosity was measured in a Brabender viscograph, type VANE H1. Five grams of each coprecipitate, or control cLBG, was dispersed in 500 milliliters of deionized water, and the mixture was stirred at 150 rpm. For the first 30 minutes, the suspension was maintained at room temperature. Then heating was begun, at a rate of 1.5° C. per minute, and was applied for about 47 minutes until the temperature of the solution reached 95° C. Next, the mixture was held for 15 min. at 95° C. Thereafter the mixture was cooled at 1.5/min. to 25°, and was held 15 min.

Inspection of the Figure shows that the control material cLBG did not significantly dissolve, as shown by the viscosity of the solution, until the solution began to be heated. Viscosity was essentially flat during the heating step, because viscosity loss due to heating approximately balanced viscosity gain due to solubilization. After cooling, the final viscosity is developed.

In contrast, the inventive 60:40 coprecipitate of LBG and konjac dissolved in the cold water, attaining approximately its final viscosity without any application of heat. As expected, viscosity was decreased during heating, and recovered on cooling. Thus the inventive coprecipitate showed the very desirable property of cold solubility, even though more than half of the inventive coprecipitate was the non-cold soluble LBG component. This ability of the dry coprocessed compositions of the invention to achieve high viscosity in cold (ambient) water results in a faster, simpler, and more efficient use of the composition. For example, in the commercial manufacture of water dessert gels, the entire process step of heating the coprocessed ingredients may be eliminated. Similarly, this property permits the formation of such desserts in the home, by merely mixing a dry coprocessed inventive gelling composition containing flavors, coloring, sweetener, and such, with ambient temperature water.

Moreover, the short hydration time achievable with the inventive coprocessed galactomannan/glucomannan compositions cannot be achieved by simple mixtures of the same ingredients in the same proportions. Without intending to be limiting by theoretical explanations, it is believed that the coprocessing of the present invention acts to intertwine the polymer chains of the ingredients, even when the inventive composition is in the form of a dry powder. Thus, upon addition of the dry powder to water, the polymer interreactive network is already set up, resulting in a marked reduction in hydration time before a desired viscosity is reached.

We claim:

1. A composition comprising:
   (A) a coprecipitate consisting essentially of:
      (a) a galactomannan, with
      (b) a glucomannan; and
   (B) optionally, a gelling agent admixed with said coprecipitate.

2. The composition of claim 1 wherein said galactomannan is locust bean gum.

3. The composition of claim 1 wherein said glucomannan is derived from konjac.

4. The composition of claim 1 wherein said galactomannan is locust bean gum and said glucomannan is derived from konjac.

5. The composition of claim 4 wherein said gelling agent is present and is carrageenan.

6. The composition of claim 1 wherein said gelling agent is present and is carrageenan, xanthan, agar, gellan, pectin, gelatin, starch, or a mixture thereof, optionally together with a gel-inducing-effective-amount of a gelling inducer.

7. The composition of claim 1 wherein all ingredients are in dry powder form.

8. The composition of claim 7 wherein said dry powder is substantially soluble in water at a temperature of about 18° to 23° C.

9. The composition of claim 1 in the form of an aqueous gel.

10. The composition of claim 1 wherein said glucomannan comprises about 10 to 90 dry wt % of said coprecipitate.

11. The composition of claim 4 wherein said glucomannan comprises about 10 to 50 dry wt % of said coprecipitate.

12. The composition of claim 4 wherein said glucomannan comprises about 20 to 40 dry wt % of said coprecipitate.

13. The composition of claim 4 wherein said glucomannan comprises about 25 to 35 dry wt % of said coprecipitate.

14. The composition of claim 6 wherein said gelling agent comprises about 10 to 90 dry wt % of said admixed composition.

15. The composition of claim 5 wherein said gelling agent comprises about 40 to 70 dry wt % of said admixed composition.

16. A method for preparing a coprecipitate of a galactomannan with a glucomannan comprising:
   (A) mixing a galactomannan with an aqueous medium to form a galactomannan sol;
   (B) mixing a glucomannan with an aqueous medium to form a glucomannan sol;
   (C) comixing the galactomannan sol and glucomannan sol if they were mixed separately;
   (D) optionally clarifying the galactomannan sol, the glucomannan sol, or their comixture;
   (E) coprecipitating the comixed sols by the addition of an organic solvent that is miscible with the aqueous medium;
   (F) separating the coprecipitate from the aqueous medium;
   (G) drying the coprecipitate, and
   (H) optionally grinding the dried coprecipitate to a powder.

17. A dry composition for a water dessert gel comprising: (A) a coprecipitate of galactomannan and a glucomannan; admixed with (B) at least one gelling agent; in further admixture with (C) an additive selected from the group consisting of colorants, sweeteners, food particles, herbs, preservatives, buffering agents, acidifying agents, gel strengtheners and mixtures thereof.

18. A water dessert gel comprising the composition of claim 17 in the form of an aqueous gel.

19. A base for a food product comprising the composition of claim 1 wherein the food product is selected from the group consisting of a gelled food, a thickened food, a pourable salad dressing, a food spread, a water dessert gel, a mayonnaise, and a frozen dessert.

20. The food product of claim 19 which is a water dessert gel.

21. A method for effecting the solubility of a galactomannan gum in water at temperatures of about 18° to 23° C. comprising coprecipitating said gum with a glucomannan gum prior to mixing it with said water.

22. The method of claim 21 wherein the glucomannan is derived from konjac.

23. The method of claim 21 wherein the galactomannan gum is locust bean gum.

24. The method of claim 21 wherein the galactomannan is derived from konjac and the glucomannan gum is locust bean gum.

25. The composition of claim 1 wherein said galactomannan is guar gum.

26. The composition of claim 1 wherein said galactomannan is tara gum.

27. The composition of claim 1 wherein said galactomannan is honey bean gum.

28. The composition of claim 1 wherein said galactomannan is lame tree gum.

29. The composition of claim 1 wherein said galactomannan is sesbania gum.

30. The composition of claim 1 wherein said galactomannan is cassia gum.

31. The process of claim 16 wherein the organic solvent of step (E) is isopropyl alcohol.

* * * * *

UNITED STATES PATENT AND TRADEMARK OFFICE
CERTIFICATE OF CORRECTION

PATENT NO. : 5,498,436
DATED : March 12, 1996
INVENTOR(S) : Modliszewski et al.

It is certified that error appears in the above-indentified patent and that said Letters Patent is hereby corrected as shown below:

Column 2, line 15, "poiysaccharide" should read --polysaccharide--.
Column 4, line 17, "Koniac" should read --Konjac--. Column 5, line
18, "tiltrate" should read --filtrate--. Column 6, line 24, "or to
1," should read --or 1 to 1,--; line 28, "Materials" should read
--Materials:--; line 60 "VANE" should read --VA/VE--.

Signed and Sealed this

Twentieth Day of August, 1996

Attest:

BRUCE LEHMAN

*Attesting Officer*   *Commissioner of Patents and Trademarks*